United States Patent
Li (10) Patent No.: US 9,603,707 B2
(45) Date of Patent: Mar. 28, 2017

(54) DIPPING MANDREL WITH A GAP

(75) Inventor: XueMei Li, Shoreview, MN (US)

(73) Assignee: St. Jude Medical, Inc., St. Paul, MN (US)

(*) Notice: Subject to any disclaimer, the term of this patent is extended or adjusted under 35 U.S.C. 154(b) by 559 days.

(21) Appl. No.: 14/235,560

(22) PCT Filed: Jul. 19, 2012

(86) PCT No.: PCT/US2012/047293
§ 371 (c)(1),
(2), (4) Date: Jan. 28, 2014

(87) PCT Pub. No.: WO2013/019416
PCT Pub. Date: Feb. 7, 2013

(65) Prior Publication Data
US 2014/0167308 A1 Jun. 19, 2014

Related U.S. Application Data

(60) Provisional application No. 61/512,999, filed on Jul. 29, 2011.

(51) Int. Cl.
*A61F 2/24* (2006.01)
*B29C 41/14* (2006.01)
*B29C 41/38* (2006.01)
*B29K 105/00* (2006.01)
*B29L 31/00* (2006.01)

(52) U.S. Cl.
CPC ............ *A61F 2/2415* (2013.01); *B29C 41/14* (2013.01); *B29C 41/38* (2013.01); *A61F 2/2412* (2013.01); *A61F 2240/005* (2013.01); *B29K 2105/0073* (2013.01); *B29L 2031/7534* (2013.01)

(58) Field of Classification Search
CPC combination set(s) only.
See application file for complete search history.

(56) References Cited

U.S. PATENT DOCUMENTS 6,953,332 B1 10/2005 Kurk et al.
7,682,389 B2 3/2010 Beith
(Continued)

FOREIGN PATENT DOCUMENTS

EP 1864687 A1 12/2007

OTHER PUBLICATIONS

International Search Report for Application No. PCT/US2012/047293 dated Oct. 30, 2012.

*Primary Examiner* — Benjamin Schiffman
(74) *Attorney, Agent, or Firm* — Lerner, David, Littenberg, Krumholz & Mentlik, LLP (57) ABSTRACT

A mandrel (5) for molding polymer valve leaflets for heart valve prostheses is disclosed, including a body portion (52) including an outer surface with ridges (60) and contoured surfaces (64) corresponding to the leaflets, the upper edge of the contoured surfaces corresponding to the free upper edge of the leaflets, and the mandrel including a mandrel extension (54) above the body portion, and a gap (68) extending around the mandrel between the upper edge of the contoured surface and the mandrel extension. A process for producing these polymer valve leaflets is also disclosed by dip coating with this mandrel and removing the polymer film created at the gap, preferably by applying suction or blowing thereto.

11 Claims, 6 Drawing Sheets

(56) References Cited

U.S. PATENT DOCUMENTS

| | | | | |
|---|---|---|---|---|
| 8,562,671 B2* | 10/2013 | Neuenschwander | . | A61F 2/2415 264/225 |
| 2014/0012371 A1* | 1/2014 | Li | ......................... | A61F 2/2415 623/2.12 |

* cited by examiner

DIPPING MANDREL WITH A GAP

CROSS-REFERENCE TO RELATED APPLICATIONS

The present application is a national phase entry under 35 U.S.C. §371 of International Application No. PCT/US2012/047293 filed Jul. 19, 2012, published in English, which claims the benefit of the filing date of U.S. Provisional Patent Application No. 61/512,999 filed Jul. 29, 2011, the disclosure of which is hereby incorporated herein by reference.

FIELD OF THE INVENTION

The present invention relates to methods for forming polymer valve leaflets for prostheses. More particularly, the present invention relates to methods for forming such valve leaflets by dip coating onto a mandrel. The present invention also relates to a mandrel for the dip coating of polymer leaflets for forming valve prostheses.

BACKGROUND OF THE INVENTION

Prosthetic heart valves with flexible leaflets, including those supported by a stent structure, are well known in the art. A variety of such prostheses are known for correcting problems associated with the cardiovascular system and in particular the heart. Therefore, the ability to replace or repair diseased heart valves with prosthetic devices has become a well-used method for treating heart valve deficiencies due to disease and congenital defects.

Prosthetic heart valve leaflets thus perform the function of opening and closing to regulate blood flow through the valve. These heart valve leaflets must therefore typically either pivot or flex with each cycle of the heart to open and close. The prostheses themselves have been constructed from natural materials such as tissues, synthetic materials, or combinations thereof. Prostheses formed from purely synthetic materials can, for example, be manufactured from biocompatible metals, ceramics, carbon materials, and polymers. In these cases, the leaflets can be either rigid or flexible in various embodiments.

Those heart valve prostheses which include flexible leaflets can be made from tissue leaflets or polymer leaflets. The use of polymer leaflets has become more desirable, particularly in accordance with the search for durable and stable leaflet performance over a number of years of use.

According to U.S. Pat. No. 6,953,332 ("the '332 Patent") and U.S. Pat. No. 7,682,389 ("the '389 Patent"), dip coating methods and mandrels are used to form these polymer leaflets and valve prostheses. Such a mandrel is shown, for example FIG. 1 hereof, which corresponds to FIG. 8 of the '332 Patent, including an upper surface 314 and a number of contours 310 which correspond to the number of valve leaflets desired. The dip coating process disclosed in the '332 and '389 Patents is one in which the mandrel itself defines the leaflet profile or shape, and after the dipping process takes place, it is generally necessary to then conduct a trimming step in order to cut the extra polymer off along the free edge of the leaflet on the mandrel (see FIG. 7). This step, in turn, requires a precisely controlled apparatus with a cutting instrument applied to the leaflet and the mandrel. This, in turn, can cause defects on the leaflet at that cutting edge and on the mandrel as well, requiring precisely machined and polished mandrel surfaces which therefore must be abandoned after the trimming step. Indeed, this also restricts the type of materials which can be used for the mandrel itself, since mandrels made of certain materials such as stainless steel would not be suitable to be applied to particular cutting instruments used thereon.

Figure 6:
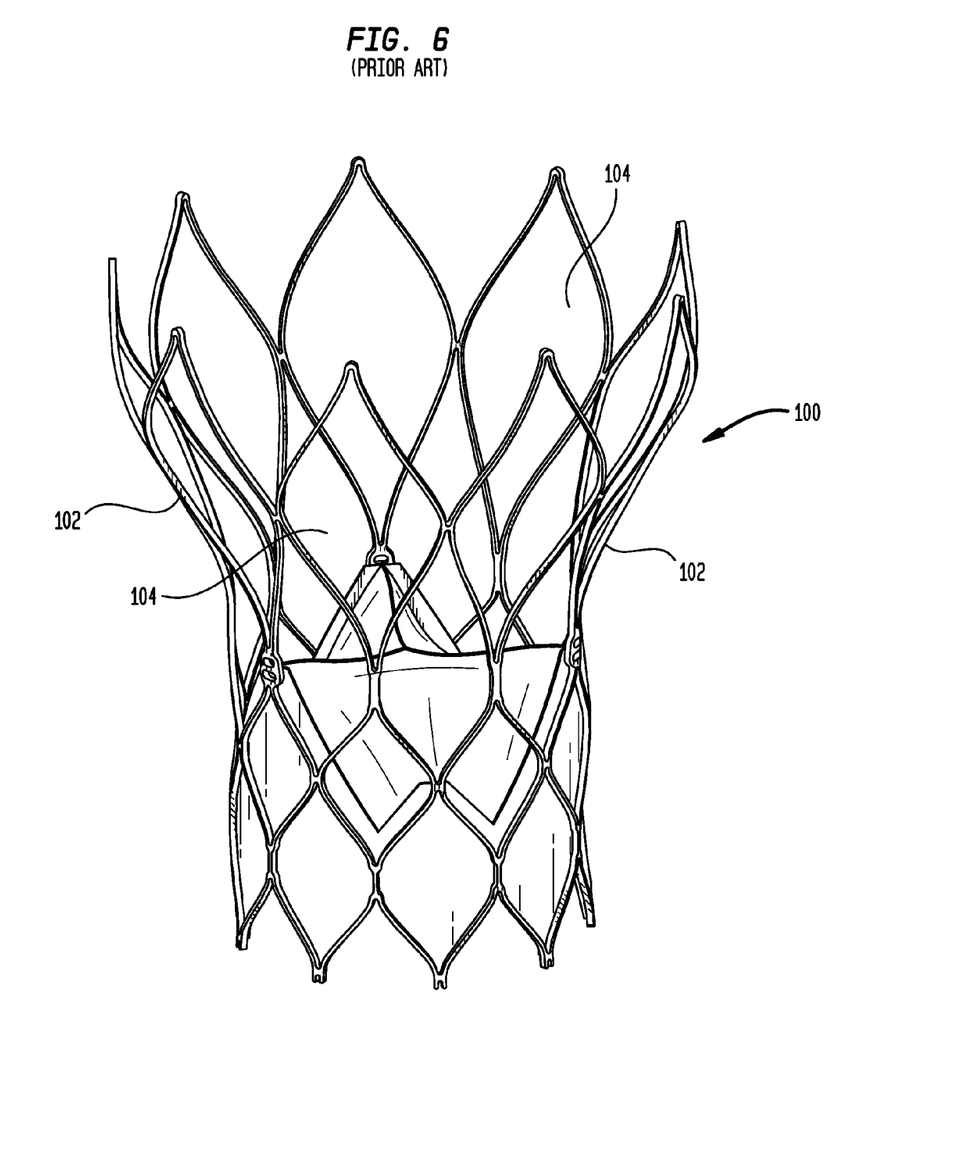
FIG. 6 is a side, perspective view of an aortic valve prosthesis with a collapsible stent, as in the prior art.

These leaflets can also be dip-coated inside an associated collapsible stent, such as those in use in connection with trans-catheter aortic valve implantation (see FIG. 6). In this case, the trimming process becomes even more difficult, particularly where the leaflet is inside the cage-like stent, as shown in FIG. 6. Since in the currently used process the leaflet cannot be trimmed inside the strut-surrounded stent, the leaflet must be preformed, trimmed, and then removed from the mandrel, and then bonded to the stent with an additional step before both the polymer of the leaflet and the polymer coated on the stent are fully cured. This therefore results in a weaker bonding force between the leaflet and the stent which cannot satisfy the functional requirements of the valve and which provide for a much more complicated manufacturing process.

The search has therefore continued for a better manufacturing process for polymer stents, particularly in connection with the mandrel dipping process, and for potential trimming processes within the stent.

SUMMARY OF THE INVENTION

In accordance with the present invention, this and other objects have not been realized by the discovery of a method for providing at least one polymer valve leaflet for a prosthesis comprising providing a mandrel including an outer surface having a plurality of ridges and at least one contoured surface between the plurality of ridges, whereby the at least one contoured surface corresponds to at least one leaflet for the prosthesis, the at least one contoured surface including an upper edge portion corresponding to the upper free edge of the at least one leaflet, the mandrel further including a mandrel extension portion above the upper edge portion including a top surface, and a circumferential gap extending around the mandrel between the upper edge portion of the at least one contoured surface and the mandrel extension portion, dipping the mandrel into a preselected polymer solution for providing the at least one leaflet, removing the mandrel from the predetermined polymer solution, removing the predetermined polymer solution from the area of the circumferential gap, curing the polymer to provide the at least one polymer valve leaflet, and removing the at least one polymer valve leaflet from the mandrel. In a preferred embodiment, the removing of the predetermined polymer solution comprises providing suction or a partial vacuum to the area of the circumferential gap, or in another embodiment applying a stream of gas to the area of the gap. Preferably, the gas comprises nitrogen or air.

In accordance with one embodiment of the method of the present invention, the at least one contoured surface comprises three contoured surfaces, and the at least one leaflet comprises three leaflets for the prosthesis.

In accordance with another embodiment of the method of the present invention, the step of removing the predetermined polymer solution from the area of the circumferential gap comprises moving a vacuum tip or a gas pressure tip circumferentially around the gap.

In accordance with another embodiment of the method of the present invention, the predetermined polymer solution comprises a synthetic polymer or a purified biological polymer. Preferably the synthetic polymer is a flexible polymer material such as polyurethane, polyurethane-silicone copolymer, poly(styrene-b-isobutylene-b-styrene), polydimethyl siloxanes, polytetrafluroethylene, and derivatives and mixtures thereof.

In accordance with another embodiment of the method of the present invention, the polymer solution includes a solvent, and the polymer solution is solidified by evaporating the solvent. Preferably, dipping of the mandrel into the preselected polymer solution comprises a plurality of dipping steps.

In accordance with the present invention, a mandrel has been discovered for the molding of a polymer valve leaflet for a prosthesis, the mandrel comprising a body portion including an upper surface having a plurality of ridges, and at least one contoured surface between the plurality of ridges, whereby the at least one contoured surface corresponds to at least one leaflet for the prosthesis, the at least one contoured surface including an upper edge portion corresponding to the upper free edge of the at least one leaflet, the mandrel further comprising a mandrel extension portion disposed above the body portion, and an intermediate circumferential gap extending around the mandrel between the upper edge portion of the at least one contoured surface and the mandrel extension portion. In a preferred embodiment, the circumferential gap includes a gap having a depth of between about 1 and 5 mm, and preferably between about 1 and 2 mm.

In accordance with another embodiment of the mandrel of the present invention, the at least one contoured surface comprises three contoured surfaces, and the corresponding at least one leaflet comprises three leaflets.

In accordance with another embodiment of the mandrel of the present invention, the body portion comprises a cylindrical body portion.

BRIEF DESCRIPTION OF THE DRAWINGS

The present invention can be more fully appreciated with reference to the following detailed description which, in turn, refers to the drawings in which.

DETAILED DESCRIPTION

The dip coating process of the present invention utilizes an improved mandrel design which has now been developed in order to facilitate the production of polymer leaflets for heart valve prostheses. The improved mandrel design in this case employs a mandrel in which a mandrel extension is provided above the upper edge of the surface of the mandrel corresponding to the free edge of the leaflets, and includes a gap between that free edge of the leaflets and the top surface of the mandrel extension.

Figure 1:
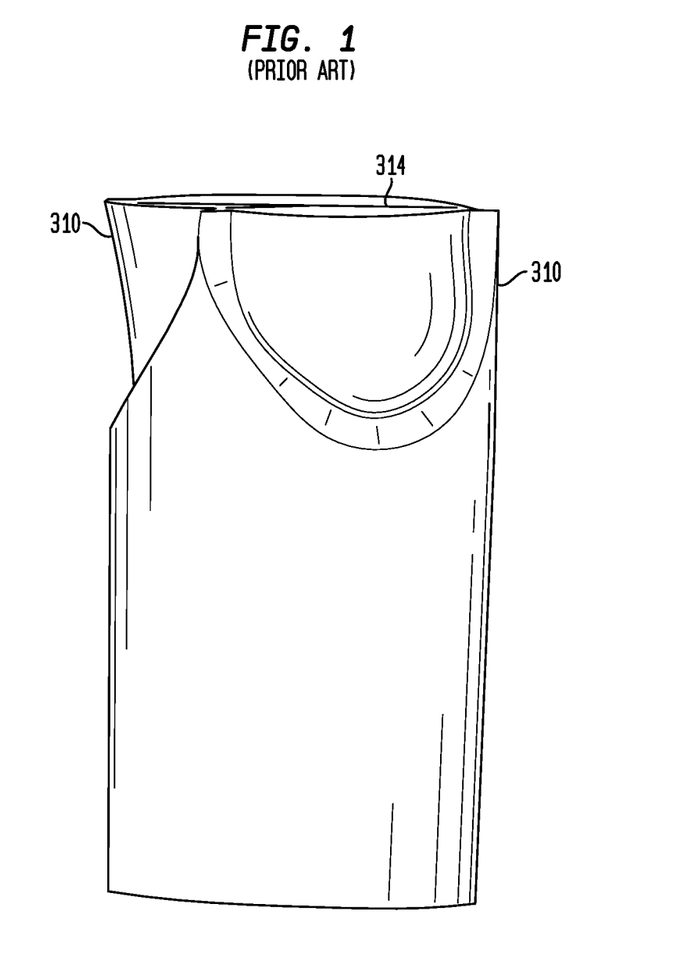
FIG. 1 is a side, elevational view of a dipping mandrel in accordance with the prior art.
Figure 7:
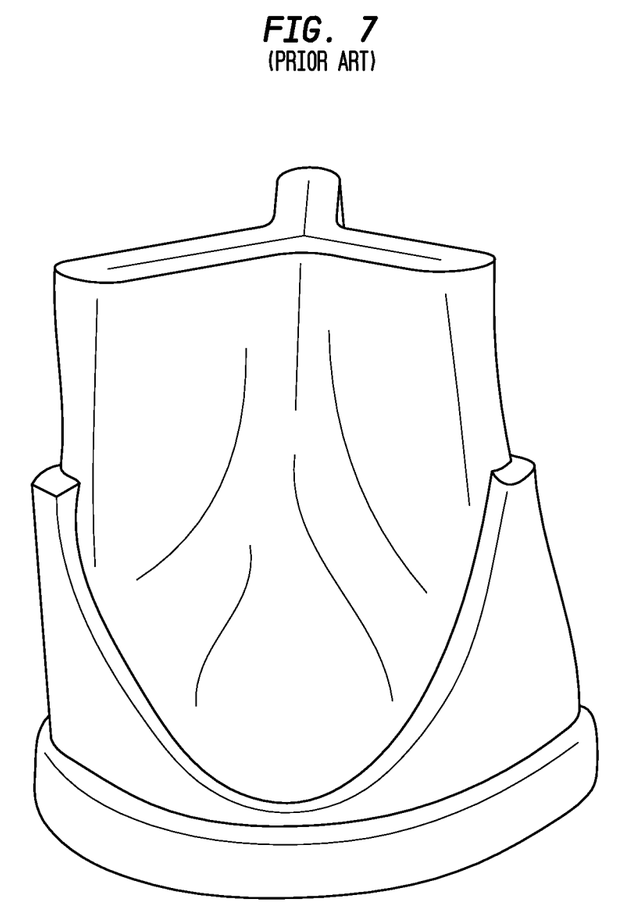
FIG. 7 is a side, perspective view of a valve prosthesis with leaflets in accordance with the prior art, in which extra polymer needs to be trimmed off.

In this manner, instead of the need to trim the upper surface of the mandrel, such as that shown in FIG. 1, or to trim extra polymer, such as shown in FIG. 7, with all of its concomitant difficulties, it is now possible to entirely eliminate such a trimming step. This is accomplished by removing polymer from the area of the gap between the lower edge of the gap corresponding to the free edge of the leaflets and the upper edge of the gap. This is facilitated by the fact that, in view of surface tension created during the dipping process, while the outer surface of the gap includes a film of the polymer, the inner surface of the gap is essentially free of polymer. It is thus possible to remove this polymer film using a vacuum, or a stream of air or other gas, in a very simple process. This, in turn, not only provides for smoother leaflets being formed, but simplifies the overall process for doing so.

The improved polymer leaflets of the present invention can then be used for the very same purposes for which they have been produced and used in the past. They can thus be used to form valve prostheses, and particularly heart valve prostheses. Damaged or diseased natural heart valves can thus be replaced with these valve prostheses in order to restore valve function. The use of polymer-formed flexible leaflets thus mimics the action of natural tissue leaflets but permits replacement of heart valves, including aortic, mitral, tricuspid, or pulmonary valves.

The leaflets of the present invention can also be used with a support structure, such as an ordinary stent (FIG. 2) or a collapsible stent (FIG. 6). The rigid support or stent thus provides a support structure for the leaflets, and generally includes commissure supports for the ends of the free edge of the leaflets and scallops/stents supporting the attached edges of the leaflets extending between the commissure supports themselves. In a preferred embodiment, the outer diameter of the mandrel is tightly mated with the inner diameter of the stent, and they are then dip-coated together. In this manner, the polymer leaflets will firmly bond with the stent.

The leaflets of the present invention are thus formed from a thin film of flexible polymer. Suitable polymers are biocompatible, in that they are nontoxic, noncarcinogenic, and do not induce hemolysis or an immunological response. Heart valve prostheses formed from polymers are preferably non-thrombogenic, and relevant mechanical properties of these polymers can include, for example, stiffness, strength, creep, hardness, fatigue resistance and tear resistance. The preferred polymers for use in accordance with the present invention are durable in that they do not significantly lose their flexibility or their mechanical strength following years of use.

The preferred process for preparing polymer leaflets is by a dip coating method using a mandrel. Thus, the mandrel surface is contoured to conform to leaflets, and a thin polymer layer is applied to the mandrel, generally by a dip coating process. The leaflets can then be removed from the mandrel in a relaxed state corresponding to a nearly closed leaflet configuration, a fully open configuration, or a partially open leaflet configuration. In any event, the leaflet shape along with its free edge is defined by the profile below the gap, and the polymer which covers the mandrel extension above the gap is discarded.

The valves include a plurality of leaflets, preferably three leaflets. They are supported by a support structure for use in either open heart surgery or trans-catheter valves.

Figure 2:
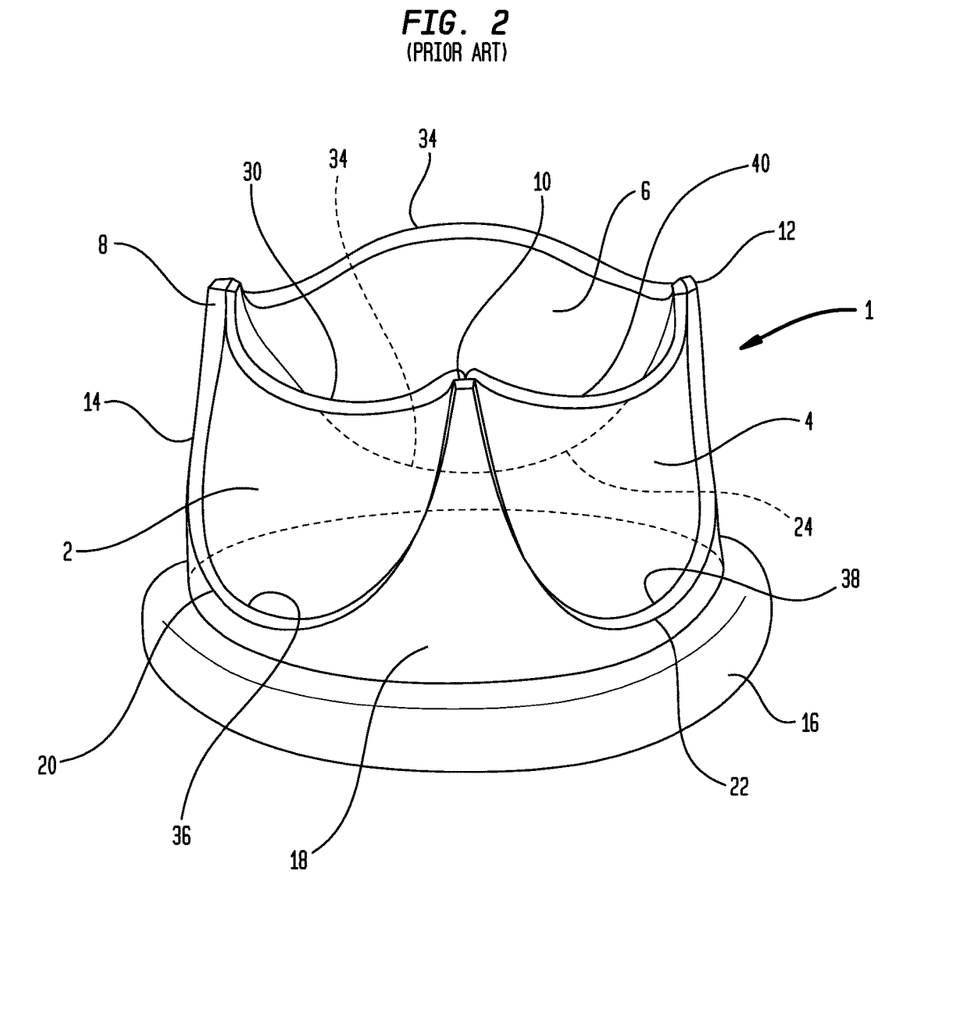
FIG. 2 is a side, perspective view of a heart valve prosthesis with the leaflets in a relaxed state, in which the valve is approximately fully open, as in the prior art.

A typical heart valve prosthesis with the leaflets in a relaxed state in an almost fully open position is shown in FIG. 2. This heart valve prosthesis 1 includes leaflets (2, 4 and 6), commissure supports (8, 10 and 12), support structure/stent (14) and sewing ring (16). The support structure/stent (14) can be relatively rigid, such that the support structure functions as a stent to maintain leaflet function with attachment to the patient at the base (18) of support structure (14). Alternatively, support structure (8) can be less rigid as part of a stentless valve, with support structure (8) being secured to other anatomical structures or other devices to maintain the leaflet function.

The support structure includes commissure supports (8, 10 and 12) and scallops (20, 22 and 24) between the commissure supports. Free edges (30, 34 and 42) of leaflets (2, 4 and 6, respectively) join at the commissure supports (10, 12 and 14). Attached edges (34, 36 and 38) of leaflets (2, 4 and 6) also attach to the support structure along scallops (20, 22 and 24). If the support structure (14) is not rigid, it should be secured to anatomical structures of other devices to maintain leaflet function.

In the case of a trans-catheter valve 100, as shown in FIG. 6, the support structure is a collapsible stent with struts 102. These struts 102 form cells 104 which thus allow the stent to be collapsed, so that it can be loaded into a catheter. The stent 100 can be self-expandable or it can be expanded by means of a balloon to be deployed in the diseased valve location in order to replace the function of the diseased valve. Once deployed, the expanding radial force generated by the self-expandable stent at its smaller diameter, as compared to its natural diameter, anchors the valve to the surrounding tissue. The balloon expandable stent is expanded by the balloon, and thus anchors to the surrounding tissue by this expanding force.

The sewing ring (16) generally extends from base (18) of the support structure (14) and facilitates attachment of the heart valve prosthesis to the patient or other components of a device. Sutures, staples, or other fastening mechanisms can be passed through the sewing cuff to secure it to the patient's tissue annulus, etc. In general, a trans-catheter valve does not require a sewing ring.

Figure 3:
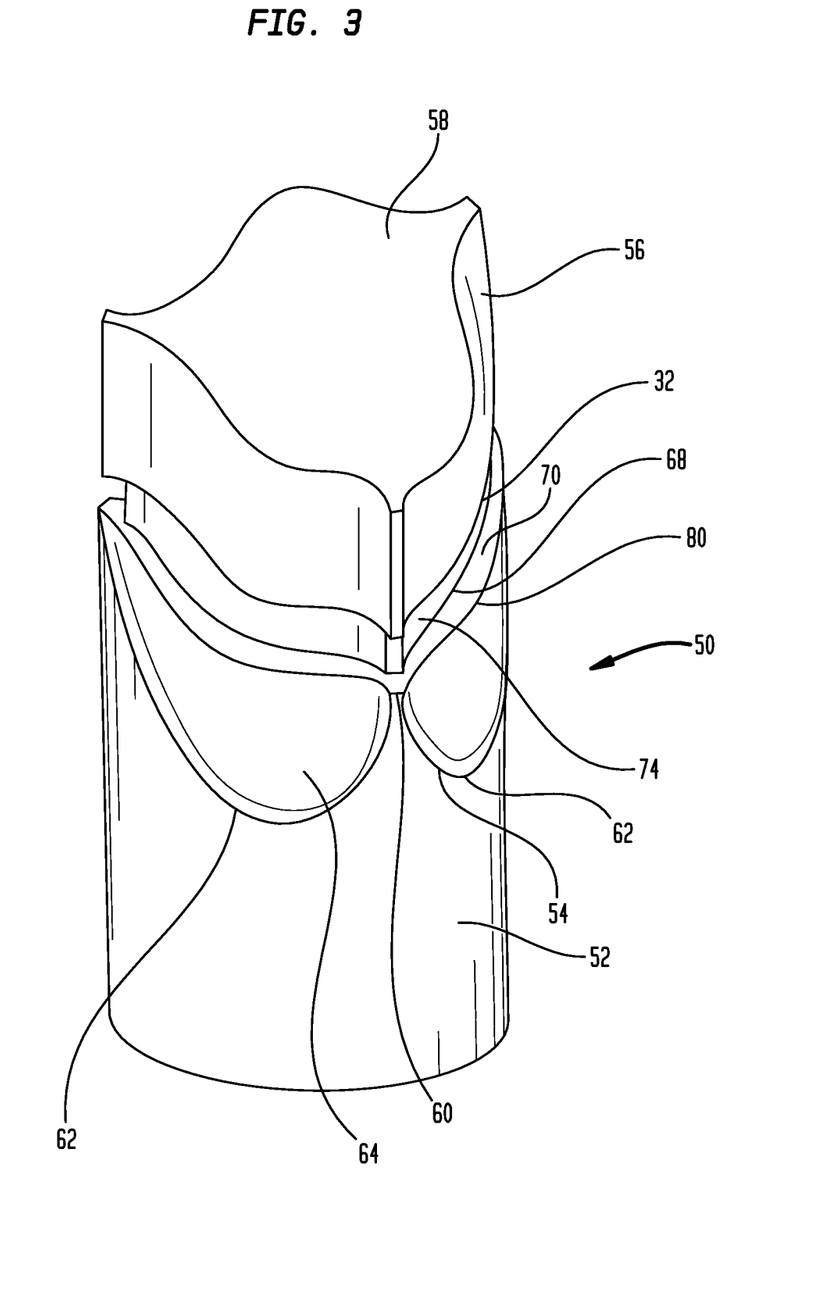
FIG. 3 is a side, perspective view of a dipping mandrel in accordance with the present invention.
Figure 4:
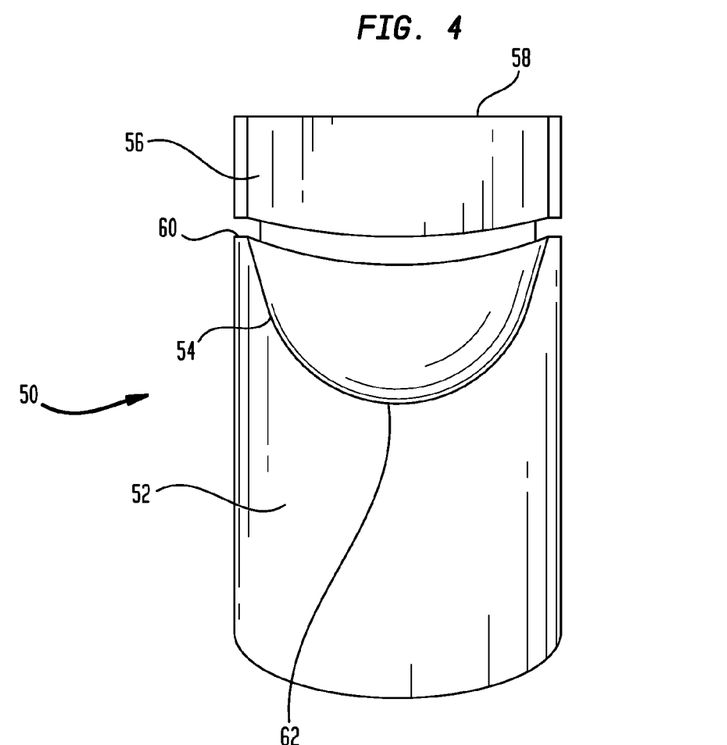
FIG. 4 is a front, elevational view of the dipping mandrel shown in FIG. 3.
Figure 5:
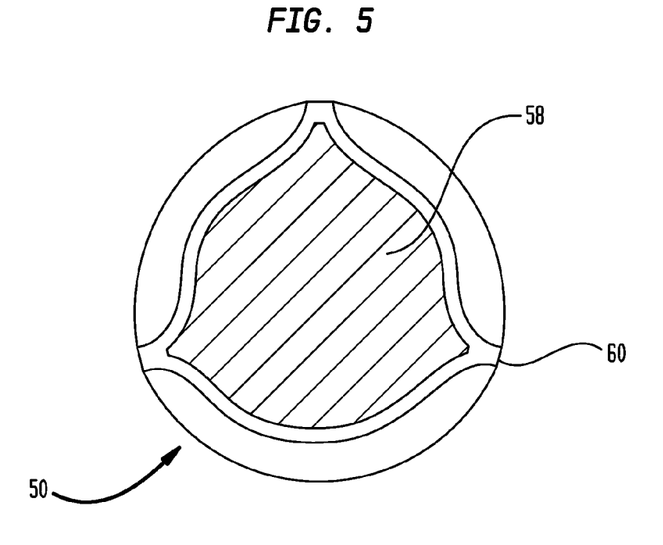
FIG. 5 is a top, elevational view of the dipping mandrel shown in FIG. 3.

Turning to FIG. 3, the improved mandrel of the present invention is shown therein. The mandrel itself (50) has a generally unitary and preferably cylindrical configuration. The mandrel (50) includes a lower shaft portion (52) leading up to the contoured portion (54). The lower shaft portion (52) is generally used to grip the mandrel (50) during the dip coating process itself. The lower shaft portion (52), while preferably cylindrical, can have other shapes and/or structural features such as appendages, holes or cavities to facilitate the gripping process. Generally, the cylindrical shaft portion (52) can be connected to an automated apparatus to lower the mandrel in a reproducible manner into the polymer coating material during the dip coating process.

The central contoured portion (54) is configured to produce structures with appropriate shapes to generate desired features in the polymer which is cast onto the mandrel surface. Above the contoured portion (54) is the dipping mandrel extension (56). This portion terminates in top surface (58) thereof. The central contoured portion (54) includes a plurality of ridges (60) which correspond to the commissure supports of the valve itself. Scalloped portions (62) connect between the ridges (60) and correspond with scallops extending between the commissure supports in the support structure. Thus, contoured surfaces (64) are formed between the ridges (60) and the scallops (62). The leaflets are thus formed on these contours (64). The attached edge of the leaflets follows the commissure support and scallops of the valve, which corresponds to ridges (60) and scallops (62) on the mandrel (50).

Above the lower shaft portion (52) and below the upper mandrel extension (56) is located a gap or groove (68). This gap (68) extends circumferentially around the entire mandrel (50) defining a separation between the upper end of the contoured portion (54) of the mandrel (50) and the lower end of the mandrel extension portion (56). The gap (68) itself thus includes a lower surface (70), an upper surface (72) and an inner indented vertical surface (74). The width of the gap (68) thus comprises a distance between the lower surface (70) and the upper surface (72), and will generally be between 0.5 and 5 mm, preferably about 1 mm. The depth of the gap (68), that is the distance from the outer surface of the mandrel (50) and the vertical wall (74) will also be between about 1 and 5 mm, preferably about 1 mm.

The edge (80) of the lower surface (70) of the gap (68) thus forms a boundary between the contours (64) and the lower surface (70) of the gap (68).

The ridges (60) thus mark the end point of the free edges of the leaflets and the separation between adjacent leaflets. These ridges (60) have various shapes to correspond to the desired valve performance characteristics. In addition, a support structure or stent can be attached to the mandrel along these ridges (60) prior to the dip coating taking place. If the polymer structure is attached to a support structure following removal from the mandrel, polymer along the ridges is associated with at least a portion of the commissure support separating adjacent leaflets. Ridges (60) help to provide proper coaptation of the closed leaflets.

The contours (64) themselves are machined (including injection molded, cast, etc.) in order to provide the desired shape for the leaflets to be ultimately produced, in their relaxed position. The leaflets have a shape approximating their fully open position. However, the leaflets can be formed in a relaxed configuration corresponding to partially closed valve positions.

In order to form the polymer leaflets, the mandrel of the present invention is preferably dip coated into a liquid polymer solution in order to cast the polymer onto the mandrel surface. The polymer is solidified on the surface of the mandrel to form a polymer structure.

Therefore, in the course of the dipping process itself, a thin film of polymer will be formed over the gap (68), and in view of surface tension formed thereon upon removal of the mandrel from the polymer solution, will not enter into the gap and/or reach the inner wall (74) thereof. Thus, in a separate process step, the removal of this thin layer or film of polymer overlying the gap (68) will eliminate the aforementioned trimming process, and result in an upper leaflet edge (a free edge) which is smooth, clear and well defined.

The step of removal of the polymer from the area of the gap (68) can comprise the application of a stream of gas such as air or nitrogen, or the application of a vacuum to remove the polymer film. This can be done by means of a pipette or with a vacuum tip before the polymer solution is fully cured. The timing which is employed in order to remove the polymer solution will depend upon the physical properties of the polymer, such as its viscosity and surface tension, so that the polymer which covers the gap can be sucked into a pipette or vacuum tip or blown out of the gap, while the polymer on the body portion of the mandrel will not continuously flow across the gap. Care must be taken so as not to damage the coated polymer on the body portion of the mandrel, such as by adjusting the strength of the vacuum applied or the pressure of the gas stream applied thereto. The thin layer of polymer which covers the gap can be removed manually using a pipette or vacuum tip or a gas stream. This thin polymer layer can also be removed automatically by the use of a robotic arm holding a vacuum tip or a gas pressure tip. Thus, one robotic arm can move circumferentially along the mandrel gap in order to remove the thin layer of polymer completely around the mandrel. On the other hand, a number of robotic arms, such as two or three, can simultaneously remove the thin layer of polymer in each of the leaflets (e.g., one for each leaflet in the case of three such arms).

Suitable polymeric materials for formation into the leaflets include, for example, synthetic polymers as well as purified biological polymers and combinations thereof. Flexible polymers include elastomers and other polymers that can sustain significant flexure, bending, twisting, wear and/or deformation without structural failure. Appropriate synthetic polymers include, without limitation, polyamides (e.g., nylon), polyesters, polyacrylates, vinyl polymers (e.g., polyolefins, polyethylene, polytetrafluoroethylene or other halogenated polymers, polypropylene, ethylene-propylene copolymers, ethylene-propylene-diene monomer copolymer (EPDM) and polyvinylchloride), polycarbonates, polyacetals (e.g., Delrin®), polyurethanes, polyurethane-silicone copolymers, poly(styrene-b-isobutylene-b-styrene), polydimethyl siloxanes, cellulose acetates, ethylene vinyl acetates, polysulfones, nitrocelluloses, derivatives thereof, similar copolymers, and mixtures thereof. Particularly preferred flexible polymer materials for the formation of flexible polymer heart valve leaflets include, for example, polyurethanes, polyurethane-silicone copolymers, poly(styrene-b-isobutylene-b-styrene), polydimethyl siloxanes, polytetrafluoroethylenes, derivatives thereof and mixtures thereof.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Preferred polymers are biocompatible. In preferred embodiments of flexible leaflets, the polymer leaflets generally have a thickness from about 50 microns to about 1000 microns and more preferably from about 100 microns to about 300 microns. A flexible polymer used to form the leaflets of heart valve prostheses is preferably a polymer that has sufficient durability to withstand the repeated cycling required for replacement heart valve use. For a human patient, the valve must cycle about 40 million times each year, and the valve ideally remains functional over the remaining natural expected lifetime of the patient. Current tissue valves may require replacement following about 400 million to about 600 million cycles. Therefore, the polymer substrate preferably can withstand at least about 400 million cycles and more preferably can withstand more than about 600 million cycles without significant structural deterioration. Polyurethanes and silicone polymers are particularly preferred for achieving these performance requirements.

The polymer leaflets flex between a generally fully open position and a generally closed position. In the open position, the free edges of the polymer leaflets form the downstream opening of the valve and do not significantly resist forward blood flow. In the closed position, the free edges of adjacent leaflets contact in the coaptation region to close the valve and do not allow significant leakage. While the leaflets flex between the open position and the closed position in use, the leaflets have a natural relaxed position when no forces are applied. When the leaflets are formed on a mandrel, the shape of the mandrel corresponds to the relaxed position of the leaflets since the polymer forms on the mandrel from a liquid without the application of any stresses to the polymer. By adjusting the shape of the mandrel, the relaxed position of the leaflets can be selected to have a desired shape.

In particular, the relaxed state of the leaflets corresponding to the mandrel shape can approximate a fully open position of the valve such that the polymer material is under little, if any, stress in the fully open position. Alternatively, the leaflets can have a relaxed position corresponding to an almost closed valve. In other alternative embodiments, the leaflets can have a relaxed position intermediate between the open position and the closed position. The processing of the valves to form the prosthesis is similar regardless of the relaxed configuration of the leaflet, except for the machining of the mandrel to produce the desired relaxed position of the leaflets.

The polymer leaflets can include one or more reinforcements to strengthen the leaflets. The reinforcement can be formed as a thickening of the flexible polymer or as an additional composition bonded to the flexible polymer forming the body of the leaflet, with or without thickening of the leaflets themselves. The reinforcement can be localized or can extend over a significant portion of the leaflet area.

As for the polymer liquid itself which is used to perform the dip coating process, these polymer solutions or dispersions comprise the above polymers dissolved or dispersed in a solvent. The solvent can be selected based on the particular polymer used. Thus, for polyurethanes, suitable solvents generally include, for example, N,N-dimethylacetamide and tetrahydrafuran. The solution concentration can be selected to yield an appropriate viscosity and coating thickness. The coating thickness will generally depend on the concentration or viscosity of the polymer solution. Desirable polymer concentration (i.e., solid content) will generally range from about 1 wt. % to about 50 wt. %, and more preferably from about 8 wt. % to about 30 wt. %.

To perform the dip coating process the mandrel is connected to an instrument that lowers the mandrel a predetermined depth into the polymer liquid. The mandrel preferably is dipped slowly into the solution to avoid significant disruption of the solution. Speed of insertion and withdrawal can also effect the coating thickness, with faster dipping resulting in a thinner polymer layer. In particular, for forming an initial polymer layer if multiple layers are applied, the first dip would preferably be slow. Actual values of dipping velocity will depend on the properties of the polymer solution.

The position of the lower edge along the base of the polymer valve structure is determined by the depth that the mandrel is inserted into the polymer liquid. If the depth of the insertion of the mandrel into the polymer liquid is controlled within a desired range, the lower edge of the polymer valve structure has a position within desired tolerances without cutting the lower edge of the structure. Generally, the mandrel is dipped at least to a position corresponding to the location at which a sewing cuff is added. However, the mandrel can be dipped to a greater depth. The dip coating can be performed manually by hand or with a mechanical device similar to a drill press to lower the mandrel by the manual rotation/movement of a lever. Alternatively, a motorized linear actuator or robot could be used to lower the mandrel into the solution. Automated dipping provides for greater control of the speed and resolution for more consistency between polymer structures. Alternatively, the mandrel and/or stent assembly can be placed inside a chamber to be filled by the polymer solution. The polymer solution can then be drained from the chamber, leaving only the coated polymer solution on the mandrel and/or stent.

Polymer coatings from polymer solutions are solidified by evaporating the solvent to leave behind the polymer. The solvent can be removed by exposure of the coated mandrel to the ambient atmosphere or, preferably, in an accelerated process by heating the coated mandrel. The coated mandrel can be heated in an oven or the like. Similarly, polymer melts coated onto a mandrel are solidified by cooling the polymer. Again, the cooling can be performed by exposing the polymer coated mandrel to the ambient atmosphere or under accelerated conditions by further cooling the coated mandrel in a refrigerator or the like.

As noted above, optional reinforcements can be placed within the polymer structure to reinforce the polymer, especially near the edge. The reinforcement material can be placed along the mandrel prior to the coating process. Alternatively, the reinforcement material can be placed over a layer of polymer after it is coated onto the mandrel. The reinforcement can be placed over the polymer prior to complete solidification or following solidification. A further polymer layer can be placed on the mandrel following placement of a reinforcing material over a polymer coat.

More than one polymer coating can be applied by dip coating in order to obtain a thicker polymer structure. Additional layers can be made using the same polymer liquid or a different polymer liquid. In particular, the polymer composition can be the same or different in a plurality of polymer liquids for dip coating. Different polymer compositions can be different with respect to chemical composition, molecular weight differences, concentrations, solvents or other features of the compositions.

Following application of all polymer coats and solidification of the polymer(s) on the mandrel, the polymer structure is separated from the mandrel. Before this takes place, however, the polymer film produced across the gap 68 must be removed. This is readily accomplished, as discussed above, by use of a vacuum or a flow of gas, such as air, or nitrogen, to remove that film before it fully cures. This is not only a simple operation, but it is one that thereby entirely eliminates the need for the far more complex trimming operation required in the past, as with the mandrel shown in FIG. 1.

In preferred embodiments the cured polymer is separated into two parts on the mandrel by means of the gap; the upper part covers the mandrel extension and the lower part covers the central contoured portion (54) and its associated stent. The upper part of the polymer can be removed, such as by tweezers or the like, and discarded. The lower part of the polymer, preferably along with its associated stent, can be carefully slid off of the mandrel, preferably in a liquid such as hot water, also preferably with the help of tweezers or the like, without damaging the polymer.

Generally, the polymer, preferably along with its associated stent, is removed from the mandrel manually. After removal from the mandrel, the polymer leaflet(s) 10 are firmly bonded with its associated stent, and an integrated valve prosthesis is thus formed. Alternatively, if the stent is not associated during the dip-coating process, the polymer valve structure separated from the mandrel can be processed into a complete prosthesis. If desired, the polymer valve structure can be stored prior to completing the prosthesis, preferably under conditions were the leaflet structures are not damaged.

Formation of Prostheses

After the leaflets are formed, additional processing steps may be needed in order to complete production of the prosthesis. In preferred embodiments, the support structure/stent is formed in association with the polymer structure during the dip coating process. In alternative embodiments in which the leaflets were not formed directly in association with a support structure/stent or if an additional support structure is desired, the polymer valve structure is connected to the support structure using, for example, a mechanical fastener, suture or adhesive. Any additional structures, such as a sewing cuff, are connected to the support structure. Sewing cuffs and the like generally are added at or near the inflow edge.

If the valve is incorporated into a conduit, the conduit can be connected to or formed around the valve such that the valve is securely connected to the conduit. Similarly, the valves can be secured within a conduit prior to attaching the conduit to remaining portions of a left ventricular assist device. Suture, staples, adhesive, and other fastening mechanisms and combinations thereof can be used to connect the support structures to the other components.

Packaging, Distribution and Use

For distribution, the medical devices are placed in sealed and sterile containers. The valves can be placed in a holder that supports the base of the valve without damaging the polymer leaflets. The containers can be dated such that the date reflects the maximum advisable storage time, if components of the medical device should not be stored indefinitely. The containers are packaged along with instructions for the proper use and/or implantation of the medical device and along with other appropriate and/or required labeling. The containers are distributed to health care professionals for use in appropriate medical procedures, such as implantation of a prosthesis and the like. Heart valve prostheses and valved vascular prostheses can be implanted, for example, using standard surgical procedures or trans-catheter apparatus.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for providing at least one polymer valve leaflet for a prosthesis comprising providing a mandrel including an outer surface having a plurality of ridges and at least one contoured surface between said plurality of ridges, whereby said at least one contoured surface corresponds to at least one leaflet for said prosthesis, said at least one contoured surface including an upper edge portion corresponding to the upper free edge of said at least leaflet, said mandrel further including a mandrel extension portion above said upper edge portion including a top surface, and a circumferential gap extending around said mandrel between said upper edge portion of said at least one contoured surface and said mandrel extension portion, dipping said mandrel into a preselected polymer solution for providing said at least one leaflet, removing said mandrel from said predetermined polymer solution, removing said predetermined polymer solution from said area of said circumferential gap, curing said polymer to provide said at least one polymer valve leaflet, and removing said at least three polymer valve leaflets from said mandrel.

2. The method of claim 1 wherein said removing of said predetermined polymer solution comprises applying suction to said area of said circumferential gap.

3. The method of claim 1 wherein said removing of said predetermined polymer solution comprises applying a partial vacuum to the area of said circumferential gap.

4. The method of claim 1 wherein said removing of said predetermined polymer solution comprises applying a stream of gas to said area of said circumferential gap.

5. The method of claim 4 wherein said gas comprises nitrogen or air.

6. The method of claim 1 wherein said plurality of ridges comprises at least three ridges and said at least one contoured surface comprises at least three contoured surfaces corresponding to said at least three ridges, whereby said at least three contoured surfaces correspond to at least three leaflets for said prosthesis.

7. The method of claim 1 where said removing of said predetermined polymer solution from said area of said circumferential gap comprises moving a vacuum tip or a gas pressure tip circumferentially around said gap.

8. The method of claim 1 wherein said predetermined polymer solution comprises a synthetic polymer or a purified biological polymer.

9. The method of claim 8 wherein said synthetic polymer comprises a flexible polymer material selected from the group consisting of polyurethane, polyurethane-silicone copolymer, poly(styrene-b-isobutylene-b-styrene), polydimethyl siloxanes, polytetrafluroethylene, and derivatives and mixtures thereof.

10. The method of claim 1 wherein said polymer solution includes a solvent, and wherein said polymer solution is solidified by evaporating said solvent.

11. The method of claim 10 wherein said dipping of said mandrel into said preselected polymer solution comprises a plurality of said dipping steps.

* * * * *